US011730778B2

(12) United States Patent
Iker et al.

(10) Patent No.: US 11,730,778 B2
(45) Date of Patent: Aug. 22, 2023

(54) METHOD OF INCREASING THE LEVEL AND PRODUCTION OF METABOLIZED PHYTONUTRIENTS IN A SUBJECT

(71) Applicant: ACCESS BUSINESS GROUP INTERNATIONAL LLC, Ada, MI (US)

(72) Inventors: Brandon C. Iker, Grand Rapids, MI (US); Matthew K. Runyon, East Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 68 days.

(21) Appl. No.: 17/028,490

(22) Filed: Sep. 22, 2020

(65) Prior Publication Data

US 2021/0085732 A1 Mar. 25, 2021

Related U.S. Application Data

(60) Provisional application No. 62/904,826, filed on Sep. 24, 2019.

(51) Int. Cl.
| | |
|---|---|
| *A61K 35/747* | (2015.01) |
| *A61K 31/7048* | (2006.01) |
| *A61K 35/745* | (2015.01) |
| *A61P 3/02* | (2006.01) |
| *A61K 31/7032* | (2006.01) |
| *A61K 31/352* | (2006.01) |
| *A61K 31/353* | (2006.01) |

(52) U.S. Cl.
CPC .......... *A61K 35/747* (2013.01); *A61K 31/352* (2013.01); *A61K 31/353* (2013.01); *A61K 31/7032* (2013.01); *A61K 31/7048* (2013.01); *A61K 35/745* (2013.01); *A61P 3/02* (2018.01)

(58) Field of Classification Search
None
See application file for complete search history.

(56) References Cited

U.S. PATENT DOCUMENTS

| | | | |
|---|---|---|---|
| 2019/0038684 A1 | 2/2019 | Uchiyama et al. | |
| 2020/0181654 A1* | 6/2020 | Yao | A61P 3/06 |
| 2020/0222474 A1* | 7/2020 | Theilmann | A61K 31/7034 |
| 2021/0038656 A1* | 2/2021 | Tripp | A61K 33/30 |

FOREIGN PATENT DOCUMENTS

| | | |
|---|---|---|
| CN | 104904859 B | 7/2018 |
| WO | 2018100776 A1 | 6/2018 |
| WO | 2019023136 A1 | 1/2019 |

OTHER PUBLICATIONS

Williamson G. et al. Role of the Small Intestine, Colon and Microbiota in Determining the Metabolic Fate of Polyphenols. Biochemical Pharmacology 139:24-39, Mar. 2017. (Year: 2017).*
Trost K. et al. Host: Microbiome Co-Metabolic Processing of Dietary Polyphenols. Food Research Int 112:108-128, Jun. 2018. (Year: 2018).*
Ladirat S. et al. High Throughput Analysis of the Impact of Antibiotics on the Human Intestinal Microbiota Composition. J of Microbiological Methods 92:387-397, Dec. 2012. (Year: 2012).*
Liu H. et al. Hesperetin Suppresses RANKL Induced Osteoclastogenesis and Ameliorates Lipopolysaccharide Induced Bone Loss. J Cellular Physiology 1-14, 2018. (Year: 2018).*
Singh B. et al. Gastrointestinal Biotransformation of Phytochemicals. Trends in Food Science & Technology 106:64-77, 2020. (Year : 2020).*
Larrosa M. et al. Anti-inflammatory Properties of a Pomegranate Extract and its Metabolite Urolithin-A in a Colitis Rat Model . . . J of Nutritional Biochemistry 21:717-725, 2010. (Year: 2010).*
Iyer N. et al. Gut Microbial Metabolite Mediated Regulation of the Intestinal Barrier in the Pathogenesis of . . . Nutrients 1-26, Nov. 2021. (Year: 2021).*
Faria A. et al. Interplay Between Anthocyanins and Gut Microbiota. J of Agricultural and Food Chemistry pp. 1-5 2014. (Year: 2014).*
International Search Report for PCT/US2020/052128 dated Jan. 14, 2021, 5 pages.
Machine assisted English translation of CN104904859B obtained from https://patents.google.com/patent on Feb. 11, 2022, 9 pages.
Amaretti, Alberto et al., "Hydrolysis of the Rutinose-Conjugates Flavonoids Rutin and Hesperidin by the Gut Microbiota and Bifidobacteria", Nutrients, vol. 7, No. 4, Apr. 14, 2015, pp. 2788-2800.
Gross, Gabriele et al., "In Vitro Bioconversion of Polyphenols from Black Tea and Red Wine/Grape Juice by Human Intestinal Microbiota Displays Strong Interindividual Variability", J. Agric. Food Chem. 2010, 58, 18, pp. 10236-10246.
Faria, Ana et al., "Interplay between Anthocyanins and Gut Microbiota", Journal of Agricultural and Food Chemistry 2014 62 (29), 6898-6902.
Andreux, P.A., Blanco-Bose, W., Ryu, D. et al., "The mitophagy activator urolithin A is safe and induces a molecular signature of improved mitochondrial and cellular health in humans." Nat Metab 1, 595-603 (2019).
Irena Krga and Dragan Milenkovic, "Anthocyanins: From Sources and Bioavailability to Cardiovascular-Health Benefits and Molecular Mechanisms of Action", Journal of Agricultural and Food Chemistry 2019 67 (7), 1771-1783.

(Continued)

*Primary Examiner* — Ralph J Gitomer
(74) *Attorney, Agent, or Firm* — Warner Norcross + Judd LLP

(57) ABSTRACT

A method useful for providing a phytonutrient to a subject via mediation of the subject's microbiome is disclosed. The method includes administering a phytofunctional composition to a subject change the phytonutrient producer status of the subject. The method may also include identifying a phytonutrient producer status of the subject by assessing a level of at least one of a preselected phytonutrient and a preselected phytonutrient precursor compound within the subject. A phytofunctional composition useful in the method is also disclosed, and comprises a phytonutrient precursor compound and an active agent. The active agent comprises a probiotic and/or a prebiotic, and is adapted to mediate production of the preselected phytonutrient in the gastrointestinal tract of the subject, thereby changing the phytonutrient producer status of the subject.

20 Claims, No Drawings

(56) References Cited

OTHER PUBLICATIONS

Setchell, Kenneth D. R. et al., "Metabolism of secoisolariciresinol-diglycoside the dietary precursor to the intestinally derived lignan enterolactone in humans", Food Funct., 2014,5,491-501.

Gong, Z., Huang, J., Xu, B. et al., "Urolithin A attenuates memory impairment and neuroinflammation in APP/PS1 mice", J Neuroinflammation 16, 62 (2019).

Gowd, V. et al., "Antioxidant and antidiabetic activity of blackberry after gastrointestinal digestion and human gut microbiota fermentation", Food Chemistry, vol. 269, Dec. 15, 2018, pp. 618-627.

Guirro, M. et al., "Metabolomics Elucidates Dose-Dependent Molecular Beneficial Effects of Hesperidin Supplementation in Rats Fed an Obesogenic Diet", Antioxidants 2020, 9, 79.

Zhou, N. et al., "Gut Microbiota: A Pivotal Hub for Polyphenols as Antidepressants", Journal of Agricultural and Food Chemistry 2020 68 (22), 6007-6020.

Hanske L, Engst W, Loh G, Sczesny S, Blaut M, Braune A., "Contribution of gut bacteria to the metabolism of cyanidin 3-glucoside in human microbiota-associated rats", Br J Nutr. Apr. 28, 2013;109(8):1433-41.

Hongming Su, Lianghua Xie, Yang Xu, Huihui Ke, Tao Bao, Yuting Li, and Wei Chen. "Pelargonidin-3-O-glucoside Derived from Wild Raspberry Exerts Antihyperglycemic Effect by Inducing Autophagy and Modulating Gut Microbiota", Journal of Agricultural and Food Chemistry 2020 68 (46), 13025-13037.

Larrosa M, González-Sarrías A, Yáñez-Gascón MJ, Selma MV, Azorln-Ortuño M, Toti S, Tomás-Barberán F, Dolara P, Espln JC., "Anti-inflammatory properties of a pomegranate extract and its metabolite urolithin-A in a colitis rat model and the effect of colon inflammation on phenolic metabolism", J Nutr Biochem. Aug. 2010;21(8):717-25.

Larrosa M, Luceri C, Vivoli E, Pagliuca C, Lodovici M, Moneti G, Dolara P., "Polyphenol metabolites from colonic microbiota exert anti-inflammatory activity on different inflammation models", Mol Nutr Food Res. Aug. 2009;53 (8):1044-54.

Liu H, Dong Y, Gao Y, Zhao L, Cai C, Qi D, Zhu M, Zhao L, Liu C, Guo F, Xiao J, Huang H., "Hesperetin suppresses RANKL-induced osteoclastogenesis and ameliorates lipopolysaccharide-induced bone loss", J Cell Physiol. Jul. 2019;234(7):11009-11022.

Laura Marin, Elisa M. Miguélez, Claudio J. Villar, Felipe Lombó, "Bioavailability of Dietary Polyphenols and Gut Microbiota Metabolism: Antimicrobial Properties", BioMed Research International, vol. 2015, Article ID 905215, 18 pages, 2015.

Zhixi Chen, Rui Zhang, Weimei Shi, Linfu Li, Hai Liu, Zhiping Liu, and Longhuo Wu. "The Multifunctional Benefits of Naturally Occurring Delphinidin and Its Glycosides", Journal of Agricultural and Food Chemistry 2019 67 (41), 11288-11306.

Sam Possemiers, Selin Bolca, Ellen Eeckhaut, Herman Depypere, Willy Verstraete, "Metabolism of isoflavones, lignans and prenylflavonoids by intestinal bacteria: producer phenotyping and relation with intestinal community", FEMS Microbiology Ecology, vol. 61, Issue 2, Aug. 2007, pp. 372-383.

Saha P, Yeoh BS, Singh R, Chandrasekar B, Vemula PK, Haribabu B, Vijay-Kumar M, Jala VR., "Gut Microbiota Conversion of Dietary Ellagic Acid into Bioactive Phytoceutical Urolithin A Inhibits Heme Peroxidases", PLoS One. Jun. 2, 2016;11(6):e0156811.

Sankaranarayanan, R.; Valiveti, C.K.; Kumar, D.R.; Van slambrouck, S.; Kesharwani, S.S.; Seefeldt, T.; Scaria, J. Tummala, H.; Bhat, G.J., "The Flavonoid Metabolite 2,4,6-Trihydroxybenzoic Acid Is a CDK Inhibitor and an Anti-Proliferative Agent: A Potential Role in Cancer Prevention", Cancers 2019, 11, 427.

Stevens, Y.; Rymenant, E.V.; Grootaert, C.; Camp, J.V.; Possemiers, S.; Masclee, A.; Jonkers, D., "The Intestinal Fate of Citrus Flavanones and Their Effects on Gastrointestinal Health", Nutrients 2019, 11, 1464.

* cited by examiner

METHOD OF INCREASING THE LEVEL AND PRODUCTION OF METABOLIZED PHYTONUTRIENTS IN A SUBJECT

CROSS-REFERENCE TO RELATED APPLICATIONS

This application claims priority to and all advantages of U.S. Provisional Application No. 62/904,826, filed 24 Sep. 2019, the content of which is incorporated herein by reference.

FIELD OF THE INVENTION

The present invention relates to methods of ameliorating microbial metabolism and, more specifically, to methods and compositions for providing phytonutrients to a subject.

BACKGROUND OF THE INVENTION

Phytonutrients are plant-derived compounds that have been associated with various health benefits in mammals (e.g. humans), including antioxidant activity, improved cardiovascular health, anti-inflammation activity, anti-aging properties, and neurological benefits. For example, polyphenol phytonutrients (e.g. flavonoids) have been positively linked to neurological benefits such as improved memory and learning behaviors in adult humans. Despite potential benefits, phytonutrients are not often used to supplement food products, as typical phytonutrients contribute undesirable colors and/or tastes to existing food/nutritional products when added thereto. As such, many phytonutrients are provided to mammals in the form of a nutritional supplement, which is typically a concentrated source of nutrients (e.g. phytonutrients) administered to provide a nutritional and/or physiological effect. However, certain phytonutrients do not natively exist (i.e., at all, or at sufficient levels) in a biologically active form, but are instead natively present in a precursor form (e.g. as a phytonutrient precursor compound). Accordingly, many phytonutrient-based nutritional supplements are ineffective or under effective due to such phytonutrient precursor compounds being unable to be adequately converted to a biologically active form, useful to the mammal's health, before being excreted by the mammal.

SUMMARY OF THE INVENTION

A method of changing a phytonutrient producer status of a subject is provided. The method is useful for mediating a subject's microbial metabolism, e.g. to maintain or improve the health or well-being of the subject. The method may include identifying the phytonutrient producer status of the subject, e.g. by assessing a level of at least one of a preselected phytonutrient and a preselected phytonutrient precursor compound within the subject. The method includes administering a phytofunctional composition to the subject, thereby changing the phytonutrient producer status of the subject. The phytofunctional composition comprises a phytonutrient precursor compound and an active agent. The active agent comprises at least one of a probiotic and a prebiotic, and is adapted to mediate production of the preselected phytonutrient in the gastrointestinal tract of the subject.

In some embodiments, the method includes identifying one or more probiotics, prebiotics, and/or phytonutrient precursor compounds to change the phytonutrient producer status of the subject.

In certain embodiments, the method includes formulating the phytofunctional composition to include the identified probiotic, prebiotic and/or phytonutrient precursor compounds before administering the phytofunctional composition to the subject.

A phytofunctional composition suitable for use in the method is also provided. In particular, the phytofunctional composition comprises a phytonutrient precursor compound adapted to be converted into or otherwise used in the production of a phytonutrient via microbial metabolism. The phytofunctional composition also comprises an active agent adapted to mediate production of a preselected phytonutrient from the phytonutrient precursor compound in the gastrointestinal tract of a subject. The active agent comprises a probiotic and/or a prebiotic.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the steps or components set forth in the following description or illustrated in the drawings. It is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE CURRENT EMBODIMENTS

The method of this disclosure is useful in providing a phytonutrient to a subject. In general, the method utilizes function-driven metagenomics to identify potential handles within complex microbial communities, and exploiting those handles to the benefit of the subject. More specifically, as will be appreciated from the description herein, the method can be useful in ameliorating a condition of the subject by providing a microbially metabolized phytonutrient thereto, e.g. via administering a phytofunctional composition to the subject to mediate the subject's microbial metabolism, thereby providing the phytonutrient to the subject with sufficiency.

Phytocompounds are chemical entities that are found in or derived from plants. Phytocompounds vary widely, and may be macromolecular, polymeric, low molecular weight, small molecules, etc. Many phytocompounds are not bioactive with respect to certain biological processes, e.g. due to being non-digestible, poorly bioavailable, and/or otherwise recalcitrant or inert to particular biological targets. However, some such phytocompounds may be transformed via microbial metabolism (e.g. by a subject's microbiome) into a form with increased bioactive against one or more biological targets. In such cases, the parent phytocompound having lower bioactivity (i.e., with respect to at least one biological target) may be referred to as a "phytonutrient precursor compound," and the bioactive metabolite thereof referred to as a "phytonutrient." While the term "phytonutrient" may conventionally be used synonymously with "phytocompound," for clarity, the term "phytonutrient precursor compound" is used herein to refer to any phytocompound, whether naturally occurring or derived from a naturally occurring composition, which may be transformed via microbial metabolism into a bioactive compound. Moreover, such bioactive compounds (i.e., those derived from microbial metabolism of a phytonutrient precursor compound) are referred to herein as "phytonutrients."

As used herein, the terms "microbiome," "microbiota," and "microbial habitat" may be used interchangeably, and refer to microorganisms in and/or on the body of a host animal (e.g. a mammal, such as a human). The microbiome can collectively comprise commensal, symbiotic, and/or pathogenic microorganisms, which are now known to exert a profound impact on the health of the host. Microbiomes can exist on or in many, if not most parts of the host. As such, specific terms may be used to refer to a localized microbiome, e.g. in or on a specific part of the host. For example, the term "gut flora" refers to microorganisms (i.e., microflora) that normally live in a gastrointestinal (GI) tract of an animal host. The gut flora present in a typical animal is highly diverse, and comprises pathogenic, benign, and beneficial microbial genera. In typical, healthy humans, the gut flora comprises beneficial bacteria such as lactobacilli and bifidobacteria, and non-beneficial gut bacteria such as bacteroides, coliforms, clostridia, and sulfate-reducing bacteria. For example, the average human colon comprises the localized microbiome with the highest degree of biodiversity in the human body, with a bacterial density estimated at around $10^{12}$ bacteria/g of colonic content composed of hundreds of individual bacterial species. Consequently, the gut flora of a given host subject, such as an individual human, can be expected to display its own characteristic metabolic profile, as described in further detail below.

Accordingly, it is to be appreciated that a given host subject's microbiome will be unique in various aspects, but will also typically share a number of similarities with microbiomes of other hosts within a given population. One such aspect is the ability, or inability, to metabolize a particular phytonutrient precursor compound into a specific phytonutrient. Said differently, in a given population, any particular subject may be able to microbially metabolize certain phytonutrient precursor compounds, but not others. For example, the phytonutrient equol is formed following the hydrolysis of the glycoside conjugates of daidzein from soy, and the methoxylated isoflavone formononetin, or its glycosidic conjugates found in clover (i.e., phytonutrient precursor compounds). Once formed, equol appears to be metabolically inert, undergoing no further biotransformation, save phase II metabolism or a minor degree of additional hydroxylation in the liver. Following the original discovery of equol's presence in urine after ingestion of soy-containing foodstuff, it was approximated from observation that from 50 to 70 percent of the adult human population did not excrete equol in urine, even upon daily administration of soy-containing foodstuff. Additionally, even when the pure isoflavone compounds are administered (i.e., absent influence from the food matrix), many people do not convert daidzein to equol. This phenomenon has led to the terminology of a person being an "equol-producer" or a "non-equol producer" (alternatively a "poor equol-producer") to describe these two distinct populations. As understood by those of skill in the art, empirical values may be assigned as "cut-off" values to differentiate between these categories. For example, subjects having plasma equol concentrations of less than 10 ng/mL (40 nmol/L) can be classified as "non-equol producers," while subjects having levels above 10 ng/mL (40 nmol/L) may thus be classified as "equol producers." Such categorizations may also be derived from levels in urine, e.g. where a subject excreting equol in a concentration of greater than 1000 nmol/L is classifies an "equol producer."

It is understood that certain phytonutrient precursor compounds that are abundantly present in foods (i.e., dietary phytocompounds) are initially absorbed in a subject's ileum, subsequently excreted as conjugates in bile, and ultimately pass through the small intestine before arriving in the subject's colon. However, it is now known that a portion of non/unabsorbed phytonutrient precursor compounds may reach a subject's colon directly after gastrointestinal passage, and thus be subjected to various microbial metabolic processes (e.g. fermentation, oxidation, deconjugation, etc.) by gut flora to provide a wide range of phytonutrients as low-molecular-weight metabolites, which may be absorbed by the host. Accordingly, the phenomenon introduced above with respect to equol may be generalized and described in terms of any particular phytonutrient being produced via microbial metabolism, with subjects being categorized as a "phytonutrient producer," a "non-phytonutrient producer," a "poor phytonutrient producer," or the like.

In some embodiments, the method includes identifying or assessing a phytonutrient-producer status of the subject. As will be appreciated from the description herein, the particular techniques and/or individual methods used in the assessment and/or identification are not particularly limited, and may be or include any suitable in vitro, in vivo, empirical, qualitative, and/or quantitative technique suitable for evaluating the presence and/or level (e.g. concentration) in the subject (e.g. directly, via sample, via representatively sample, etc.) of a particular phytonutrient, a metabolite or metabolic precursor thereof (e.g. a corresponding phytonutrient precursor compound), or an active agent capable of producing any of the preceding or other quantifiable markers of phytonutrient-producer status (collectively, "biomarkers"). However, it is also to be appreciated that, in some embodiments, the phytonutrient-producer status of an individual subject need not be identified or assessed directly prior to administering the phytofunctional composition thereto. Rather, the phytofunctional composition may be formulated based on an assessment of common phytonutrient-producer statuses (e.g. globally, or within a particular population) and provided to a subject on the basis of an association therewith. As such, while the method may be utilized to provide individualized prophylactic effects to a particular subject, it may also be utilized on a basis of capability to providing prophylactic effects to a portion of a given population (e.g. as a general supplement for potential metabolic support, as described in further detail below).

The subject is not limited, and may be any organism with a microbiome. Typically, however, the subject is an animal, such as a mammal (i.e., vertebrates of the class Mammalia, such as dogs, cats, goats, sheep, pigs, cattle, horses, donkeys, camels, and the like). Additional mammals that are specifically contemplated herein include semi-domesticated mammals and mammals that are routinely bred in captivity. Of course, the term mammal also encompasses humans (which may be referred to as "people" and/or "person(s)"). When describing a human, the term "adult" is typically used herein to refer to a human that has reached sexual maturity. By contrast, the terms "child" and "juvenile" are used herein to refer to a human that has not yet reached sexual maturity. Typically, the term "child" means a human subject between the stage of birth and the age of about 10 (i.e., childhood), and the term "juvenile" means a human subject that is greater than the age of about 10 and who has not completed the stage of puberty. Of course, the terms child, juvenile, adult, and infant are all encompassed by the term human, which is itself a subcategory of mammal, which is a subcategory of animal as defined herein.

Any evaluation technique may be utilized, such as urinalysis, fecal analysis, blood plasma analysis, tissue analysis, saliva analysis, etc., or combinations thereof. Moreover, such techniques may be individualistic (i.e., tailored to one or more specific markers) or systems-level in scope, such as those involving multiomic technologies suitable for identifying biomarkers in one or more tissues of other biological materials of the subject (e.g. blood, urine, sweat, saliva, fecal matter, etc.). Moreover, such evaluations may direct or indirect in nature, such as those assessing a sample for a particular biomarker (i.e., direct evaluations) as well as those assessing a characteristic or property indicative of a biomarker related to phytonutrient-producer status. For example, direct metabolomic, proteomic, and/or genomic analyses may also be utilized. Additionally, physical indicators (i.e., rather than biological indicators) may also, or alternatively be utilized. For example, Bristol stool scores indicative of constipation (e.g. harder stool) have been shown to be associated with higher Shannon diversity, i.e., an α-diversity metric summarizing taxonomic richness and evenness, which is increasingly reported in the gut microbiome literature and may be used as a marker for microbiome health. As such, physical indicators such as hard stool or loose stool, Bristol scores or other descriptive, qualitative, and/or quantitative measurements used to describe such stool, metrics associated with such measurements, or even population data (e.g. obtained via sample collection, survey, etc.) evidencing the presence or likelihood of such a metric, measurement, or physical indicator, may be used to identify or evaluate the phytonutrient-producer status of the subject.

Accordingly, it will be understood by those of skill in the art that evaluations concerning the phytonutrient-producer status of the subject may comprise conducting a trial, study, and/or a model-based experiment, such as those described in greater detail below. In certain embodiments, assessing the phytonutrient-producer status of the subject comprises performing a high-throughput analysis or screening. In these or other embodiments, assessing the phytonutrient-producer status of the subject comprises utilizing a microbiota-representing microarray, such as an intestinal or colonic microbiota-representing microarray. Such microarrays may be adapted from those known in the art, which typically utilize commercially available materials.

For example, in certain embodiments, the method comprises performing a fermentation by culturing a microbiota sample obtained from the subject, incubated with a phytonutrient precursor compound. The fermentation may be performed with a culture model, such as an in vitro gut model (i.e., a model representative of human colonic microbiota that simulates microbial processes in a human large intestine). In some embodiments, the fermentation is performed as a batch fermentation using fecal samples. As will be understood by those of skill in the art, such assays provide for efficient comparison of microbial fermentation processes of different human microbial communities via use of metabolite profiling methods under conditions simulating those present in the distal colon. Regardless of the particular fermentation technique utilized, the evaluation typically comprises monitoring the presence and, optionally, the amount of phytonutrients being prepared during the fermentation (e.g. as breakdown products). Such monitoring may be performed by various metabolite profiling techniques known in the art, such as via nuclear magnetic resonance (NMR)-based metabolite profiling, gas chromatography-mass spectrometry (GC-MS)-based profiling, and the like, as well as combinations thereof.

In some embodiments, assessing the phytonutrient-producer status of the subject is further defined as evaluating the functional capacity of the subject's gut microbiota. In particular, it is believed that beneficial effects obtained by ingestion of certain foods are dependent on biotransformation of phytocompounds by intestinal bacteria to bioactive metabolites, i.e., to provide certain phytonutrients from phytonutrient precursor compounds. It is to be appreciated that the underlying mechanisms and bacterial species involved in such phytonutrient production have not yet been fully identified, and the bacterial metabolism of complex mixtures of phytocompounds present in the human diet has been studied far less extensively than that of single compounds. However, as is demonstrated herein, it is believed that differences in phytonutrient-producer status may be attributed to differences in the metabolic potential of endogenous microbiota in a given subject.

In certain embodiments, assessing the phytonutrient-producer status of the subject comprises quantifying the amount of a particular phytonutrient present in the subject, which is typically expressed as a relative concentration (e.g. a blood concentration level, a urine concentration level, etc.). It is to be appreciated that the excretion of particular phytonutrients may be highly variable among individuals, and thus there may a small or large demarcation between producers and non-producers of a given phytonutrient. As such, in certain embodiments, assessing the phytonutrient-producer status of the subject comprises comparing a biological concentration and/or excretion amount of a phytonutrient of the subject against commensurate measurements obtained from other subjects. Such commensurate measurements may be obtained directly or indirectly, e.g. via population sample, survey, averaging, etc. In some embodiments, the method comprises determining empirical cut-off values for biological concentration and/or excretion of any particular phytonutrient, or a collective amount of multiple phytonutrients within a grouping, to differentiate between categories of production statuses (e.g. producers vs. nonproducers) for those phytonutrient(s). In such embodiments, comparing the biological concentration and/or excretion amount of a phytonutrient of the subject against commensurate measurements obtained from other subjects may comprise, or otherwise be performed by, comparing the subject's phytonutrient content against the cut-off value and thereby classifying the subject as a producer or non-producers for a given phytonutrient.

The particular phytonutrient assessed is not limited. Rather, the present method may be used with regard to any phytonutrient that is produced in vivo via microbial metabolism of a phytonutrient precursor compound in a subject. Moreover, any number of phytonutrients and/or phytonutrient precursor compounds may be assessed, administered, or otherwise utilized in the present method. Certain general examples of phytonutrients include dietary carbohydrates (e.g. resistant starches), lipids (e.g. omegas 3, 6, etc.), proteins (e.g. whole, isolates, hydrolysates, etc., from soy, whey, rice, pea, etc.), phenylpropanoids (i.e., aromatic compounds comprising a phenylpropane moiety), pteridines, benzopyrans, benzenoids, lignans, neolignans, and the like, as well as derivatives, modifications, and combinations thereof. For example, such phytonutrients may comprise proteins, peptides, complex amino acids (e.g. those found in plant or animal-based protein isolates from whey, egg, soy, rice, wheat, pulses, algae, fungus, peas, potatoes, fruit, buckwheat, corn, etc.), branch chain amino acids, medium- and short chain fatty acids (e.g. caproic acids, caprylic acids, capric acids, lauric acids, isovaleric acids, valeric acids, isobutyric acids, butyric acids, propionic acids, acetic acid, formic acid, etc.), hydroxyl acids (e.g. lactic acid, etc.), and the like, as well as derivatives, modifications, and combinations thereof. Some examples of phytonutrients include phenylpropanoic acids, flavonoids (i.e., compounds comprising a 2-phenylchromene moiety), isoflavonoids (i.e., compounds including a 3-phenylchromen-4-one moiety or a moiety derived therefrom), hydroxyisoflavonoids (i.e., hydroxyl-functional isoflavonoids), isoflav-2-enes (i.e., compounds comprising a 3-phenylchromene moiety having a chromenyl C2-C3 alkene), flavanones (i.e., compounds comprising a flavan-3-one moiety, including those comprising a 2-phenyl-3,4-dihydro-2H-1-benzopyran bearing a C3 ketone), isoflavones (i.e., polycyclic compounds comprising a C4-ketonyl 2-isoflavene moiety), flavans (i.e., compounds comprising a 2-phenyl-3,4-dihydro-2H-1-benzopyran moiety), coumarins (i.e., compounds comprising a 1-benzopyran-2-one moiety), isocoumarins (i.e., C1-ketonyl isochromanes), pterins (i.e., polycyclic aromatic compounds comprising a pterin moiety), chromones (i.e., compounds comprising a benzopyran-4-one moiety), phenols (e.g. benzenediols such as catechols), dibenzylbutane lignans, dibenzylbutanediol lignans and the like, as well as derivatives, modifications, and combinations thereof. Specific examples of phytonutrients may include: 2-(4-hydroxyphenyl)propionate; 2,3-dehydroequol; 2,4,6-trihydroxybenzaldehyde; 2,4,6-trihydroxybenzoic acid; 3-(3,4-dihydroxyphenyl)-acetic acid; 3-(3,4-dihydroxyphenyl)propionate; 3-(3-hydroxyphenyl)-propionic acid; 3-(4-hydroxyphenyl)propionate; 3,4-dihydroxybenzoic acid; 3,4-dihydroxybenzyldehyde; 3,4-dihydroxyphenylacetaldehyde; 3,4-dihydroxyphenylacetate; 3,4-dihydroxyphenylenolpyruvate; 3,4-dihydroxyphenylpyruvate; 4-hydroxyphenylacetate; 5-(3',4'-dihydroxyphenyl)-y-valerolactone; 5-(3',5'-dihydroxyphenyl)-y-valerolactone.; 6'-hydroxy-O-desmethylangolensin; acetate; alpha-2',3,4,4',6'-hexahydroxydihydrochalcone; alphitonin; butyrate; daidzein; dihydrodaidzein; enterodiol; enterolactone; equol (e.g. (S)-equol); eriodictyol; ethanol; formate; genistein; glucose; hemoeriodictyol; hesperetin; lactate; 0-desmethylangolensin; phenylacetate; phloroglucinol; protocatechuic acid; quercetin; sulfurophane; taxifolin; tetrahydrodaidzein; urolithin A (e.g. 3,8-dihydroxybenzo[c]chromen-6-one), and the like, as well as derivatives, modifications, and combinations thereof. However, it is to be understood that other phytonutrients, including those derived from the phytonutrient precursor compounds described herein, may be assessed as alternatives to, or in addition to, any of those described above.

In certain embodiments, assessing the phytonutrient-producer status of the subject comprises determining the presence and/or amount of a phytonutrient within, or being excreted by, the subject, where the phytonutrient comprises: protocatechuic acid; 3-(3,4-dihydroxyphenyl)-acetic acid; 3-(3-hydroxyphenyl)-propionic acid; 3,4-dihydroxybenzoic acid; 2,4,6-trihydroxybenzaldehyde; 2,4,6-trihydroxybenzoic acid; eriodictyol; hemoeriodictyol; hesperetin; parargonidin-3-O-glucoside; urolithin A (e.g. 3,8-dihydroxybenzo[c]chromen-6-one); (S)-equol; 0-desmethylangolensin; enterodiol; enterolactone; sulfurophane; 5-(3',4'-dihydroxyphenyl)-y-valerolactone; 5-(3',5'-dihydroxyphenyl)-y-valerolactone; dihydrocaffeic acid; isoferulic acid; 4-hydroxyphenylacetic acid; dihydroferulic acid, ferulic acid; resorcinol; phloroglucinol; 2,4-dihydroxyphenylacetic acid; 4-hydroxybenzoic acid; phloretic acid; phloroglucinic acid; hydrocinnamic acid; protocatechuic acid; and/or hippuric acid.

The method includes administering to the subject a composition to ameliorate the phytonutrient-producer status of the subject. As such, the method provides a means to overcome the subject's lack of in vivo production of one or more particular phytonutrients, such as those described herein. As will be understood from the description below, the phytofunctional composition may increase the functional capacity of the subject's native gut microbiota (e.g. via stimulation of the microbes therein), supplement the functional capacity subject's gut microbiota (e.g. by providing additional microbial species and/or altering the population ratios thereof), and/or circumvent certain microbial metabolic processes (e.g. by providing phytonutrient precursor compounds that do not require certain microbially-mediated transformations, thereby bypassing certain metabolic requirements). Regardless of the mechanism, administering the phytofunctional composition to the subject typically results in the production of a phytonutrient from a phytonutrient precursor compound (e.g. via microbial metabolism). In certain embodiments, administering the phytofunctional composition results in an increase in the production of the phytonutrient in an amount of from greater than 0 to 1000, alternatively of from greater than 0 to 500, alternatively of from greater than 0 to 200, alternatively of from greater than 0 to 100, %, as compared to the production of the phytonutrient in a non-producer not having been administered the phytofunctional composition. In these or other embodiments, administering the phytofunctional composition results in an increase in the production of the phytonutrient in the subject in an amount of from greater than 0 to 5000, alternatively of from greater than 0 to 2500, alternatively of from greater than 0 to 1000, alternatively of from greater than 0 to 750, alternatively of from greater than 0 to 500, alternatively of from greater than 0 to 250, alternatively of from greater than 0 to 200, alternatively of from greater than 0 to 150, alternatively of from greater than 0 to 100, alternatively of from greater than 0 to 75, alternatively of from greater than 0 to 50, alternatively of from greater than 0 to 40, alternatively of from greater than 0 to 30, alternatively of from greater than 0 to 25, alternatively of from greater than 0 to 20, alternatively of from greater than 0 to 15, alternatively of from greater than 0 to 10, alternatively of from greater than 0 to 5, nmol/L. In such embodiments, the particular amount of phytonutrient produced may vary, e.g. based on the amount of the phytofunctional composition administered, the producer status of the subject, the particular phytonutrient being assessed, etc. As understood by those of skill in the art, the increase in production of the phytonutrient may be measured using various techniques (e.g. urinalysis, fecal analysis, blood plasma analysis, etc.), which may be used to quantify the level of the phytonutrient itself, or a metabolite of the phytonutrient (e.g. as present in the subject's urine, blood, etc.). It is to be appreciated that administration of the phytofunctional composition may be used to supplement in vivo production in phytonutrient producers, non-phytonutrient producers, and poor phytonutrient producers alike.

Many phytonutrients mediate a particular therapeutic and/or prophylactic effect, and thus may be used to treat or ameliorate a condition in a subject. As used herein, the terms "treatment" or "treating" may be used interchangeably, and refer to an approach for obtaining beneficial or desired results including but not limited to a therapeutic benefit and/or a prophylactic benefit. A therapeutic benefit can mean eradication or amelioration of the underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

In general, the method may include or be used to ameliorate conditions such as those above, i.e., by mediating the production (e.g. via microbial metabolism) of the phytonutrient in the subject, where the phytonutrient mediates an effect in the subject. For example, in certain embodiments, the method may be used to ameliorate a condition via anti-inflammatory, antioxidant, anti-bacterial, autophagy, mitochondrial, intestinal barrier, microbiota composition, immune, neurologic, and/or anti-aging effects. In these or other embodiments, the method may be used to ameliorate a condition affecting a subject's endurance, heart health, skin health, insulin sensitivity, eye health, cognition (e.g. memory), liver health, elevated cholesterol, hormone balance, reproductive health, and/or digestive health. For example, the method may be used to ameliorate such a condition by improving visual function, reducing inflammation (e.g. via inhibiting proinflammatory enzymes such as lipoxygenase (LPO) and cyclo-oxygenases (COX-1, COX-2)), reducing oxidant concentration, increasing vasodilation, controlling blood glucose and/or lipid levels, inhibiting a stage of a cancer process (e.g. by increasing apoptosis and/or decreasing metastasis, signal transduction, transcription factor activity, cell adhesion, etc.), and the like, or combinations thereof.

In view of the above, it is to be appreciated that the particular biological effects imparted to the subject via mediating the production of the phytonutrient are not limited, and may be diverse and varied in terms of mechanism of action and overall health benefits conferred to the subject. For example, in some embodiments, the method includes mediating the production of 2,4,6-trihydroxybenzoic acid (2,4,6-THBA) (i.e., the phytonutrient) from cyanidin-3-glucoside (i.e., the phytonutrient precursor compound) to influence a biological process involving cyclin dependent kinase (CDK 1,2,4) and/or cell proliferation, thereby ameliorating a condition involving colorectal cancer. In these or other embodiments, the method includes mediating the production of short-chain fatty acids, parargonidin-3-O-glucoside, and/or another phytonutrient from an anthocyanin (i.e., the phytonutrient precursor compound) to influence gut barrier function, autophagy, or a biological process involving MAPK, and/or NF-kb, thereby ameliorating a condition involving gut barrier function, cellular aging, neuroprotection, and/or hyperglycemia.

In these or other embodiments, the method includes mediating the production of a phytonutrient from delphinidin (i.e., the phytonutrient precursor compound) to influence a biological process involving CBRs, ERα/β, EGFR, BCRP, and/or SGLT-1, thereby ameliorating a condition involving cardiovascular health, neuroprotection, and/or hyperglycemia. In these or other embodiments, the method includes mediating the production of hesperitin, dihydrocaffeic acid, isoferulic acid, 4-hydroxyphenylacetic acid, dihydroferulic acid, ferulic acid, resorcinol, phloroglucinol, 2,4-dihydroxyphenylacetic acid, 4-hydroxybenzoic acid, phloretic acid, phloroglucinic acid, hydrocinnamic acid, 3-(3'-hydroxyphenyl)propionic acid, protocatechuic acid, and/or hippuric acid (i.e., the phytonutrient) from hesperidin and/or naringin (i.e., the phytonutrient precursor compound) to influence a biological process involving RANKL-induced osteoclastogenesis, SOFA production, transepithelial electrical resistance TEER, and/or Claudin, thereby ameliorating a condition involving bone loss due to leaky gut, intestinal barrier function, gastrointestinal inflammation, and/or metabolic syndrome (MetS). In these or other embodiments, the method includes mediating the production of hydrocaffeic (HCAF), dihydroxyphenyl acetic (dOHPA), and hydroferulic acid (HFER) (i.e., the phytonutrient) from a polyphenol (i.e., the phytonutrient precursor compound) to influence a biological process involving levels of cytokines IL-1β, IL-8, and TNF-α, levels of malonyldialdehyde (MDA), and/or oxidative DNA damage (e.g. measured as 8-oxo-2'-deoxyguanosine levels) in distal colon mucosa, thereby ameliorating a condition involving inflammation. In these or other embodiments, the method includes mediating the production of urolithin A (i.e., the phytonutrient) from ellagic acid (i.e., the phytonutrient precursor compound) to influence a biological process involving decreased inflammation markers (iNOS, cycloxygenase-2, PTGES and PGE(2) in colonic mucosa), Mitochondrial function, UA attenuated Aβ deposition, peri-plaque microgliosis and astrocytosis in the cortex and hippocampus, AMPK activation, activation of P65NF-κB and P38MAPK, and/or Bace1 and APP degradation, thereby ameliorating a condition involving neuro and/or colonic inflammation, skeletal muscle health, cellular aging, and/or memory impairment. In these or other embodiments, the method includes mediating the production of a phytonutrient from an anthocyanin (i.e., the phytonutrient precursor compound) to influence a biological process involving high glucose, palmitic acid-induced ROS overproduction, mitochondrial membrane collapse, and/or glutathione depletion in HepG2 cells, thereby ameliorating a condition involving oxidative stress/damage and/or diabetes (e.g. via antidiabetic activity).

The phytofunctional composition may be administered as needed, daily, several times per day or in any suitable regimen such that the desired outcome is achieved. In the methods, the frequency of administration can depend on several factors, including the desired level of prevention or amelioration. Generally, a regimen includes administration of the phytofunctional composition to the subject once or twice daily, e.g. to include an administration in the morning and/or an administration in the evening. The amount of composition administered to the subject during each administration may depend on several factors including level of desired results and the specific composition being utilized. In general, the phytofunctional composition is administered in a therapeutically or physiologically effective amount. As used herein, the term "therapeutically effective amount" relates to an amount (i.e., a quantity) of a composition (e.g. the phytofunctional composition of the present embodiments) required to achieve a particular therapeutic and/or prophylactic effect, such as in treating a patient. Likewise, as used herein, the term "physiologically effective amount" relates to an amount of a composition required to achieve a desired physiological effect. Such effective amounts are typically measured and/or expressed in terms of g/day, or a derivative thereof (e.g. mg/day). Typically, the phytofunctional composition is administered in an amount effective to provide the phytonutrient to the subject. In certain embodiments, the phytofunctional composition is administered in an amount effective to change or ameliorate the phytonutrient-producer status of the subject. In these or other embodiments, the phytofunctional composition is administered in an amount effective to ameliorate a medical condition of the subject.

In general, the phytofunctional composition utilized in the method is not limited in terms of formulation, peripheral ingredients, form, or number of functions. Rather, the phytofunctional composition may be varied, and many be formulated in any fashion consistent with this disclosure. As introduced above, the phytofunctional composition is utilized in the method to confer a health benefit to the subject, such as by ameliorating the subject's phytonutrient-producer status regarding a particular phytonutrient or a disease/disorder relating thereto.

The phytofunctional composition comprises an active agent. The active agent is not limited, and may be any agent suitable for ameliorating the phytonutrient-producer status of the subject. Typically, the active agent comprises, alternatively is, a probiotic, a prebiotic, and/or a phytonutrient precursor compound.

In some embodiments, the active agent is or comprises the probiotic. The term "probiotic" as used herein can mean one or more microorganisms which, when administered appropriately, can confer a health benefit on the host or subject. As such, in certain embodiments, the phytofunctional composition comprises a population of microorganisms. The microorganism(s) of the probiotic may be obtained in various ways. In certain embodiments, a sample of a population is collected from human fecal samples and subsequently cultivated and processed into the probiotic. Examples of suitable probiotics typically include members of the Coriobacteriaceae family and/or the *Clostridium coccoides-Eubacterium rectale* cluster, as well as various *Lactobacillus* sp. and *Bifodobacterium* sp. Some examples of suitable probiotics include those of family Bacteroidaceae, Clostridiaceae, Prevotellaceae, Eubacteriaceae, Rum inococcaceae, Bifidobacteriaceae, Lactobacillaceae, Enterobacteriaceae, Saccharomycetaceae, Methanobacteriaceae, and the like, or combinations thereof. Some particular examples include: *C. orbiscidens; Eubacterium; oxidoreducens; B. subtilus; Bacteroides distasonis; Bacteroides uniformis; Bacteroides ovatus; Enterococcus casseliflavus; Eubacterium ramulus; Lactobacillus-Enterococcus*; Lachnospiraceae; *L johnsonii; Bifidobacterium catenulatum; Bifidobacterium pseudocatenultum; Gordonibacter urolithinfaciens; Gordonibacter pamelaeae; Clostridium coccoides; Clostridium leptum; Streptococcus intermedius; Ruminococcus productus; Eggerthella* sp. Julong 732; *Enterococcus faecium* EPI1; *Lactobacillus* mucosae EPI2; *Finegoldia magna* EPI3; *Feacalibacterium; Slackia isoflavoniconverten;* and *Eggerthella* sp.; as well as various derivatives and/or combinations thereof.

In certain embodiments, the active agent is or comprises the prebiotic. The term "prebiotic" as used herein refers to a compound, or a combination of compounds, that is not digestible by the subject (e.g. an animal), but which may selectively stimulate the growth and/or activity of one or a limited number of beneficial bacteria in the microbiome of the subject. Additionally, the term "prebiotic effect" refers to a selective, prebiotic-induced stimulation of growth and/or activity of one or a limited number of bacteria (e.g. bifidobacteria, lactobacilli, etc.) in the microbiome of the host. In general, the prebiotic is not limited, and may be any compound or combination of compounds that stimulate the growth of one or more microbes in the microbiome of the host, including those exemplified herein with respect to the probiotic. The prebiotic may stimulate such growth directly (e.g. by providing nutrients to the microbes) and/or indirectly (e.g. by preventing growth of competing microbes). Examples of suitable prebiotics typically include fibers, such as soluble fibers (i.e., those which dissolve in water) and insoluble fibers (i.e., those which do not dissolve in water). Some examples of fibers include starch, non-starch polysaccharides and oligosaccharides, carbohydrate fibers, lignans, and the like, as well as combinations thereof. Specific examples of suitable fibers for use in or as the prebiotic include cellulose, hemicellulose, arabinoxylans, polyfructose, inulin, oligofructans, galacto-oligosaccharides, gums, mucilages, pectins, dextrins, malodextrins, synthetic carbohydrates, polydextrose, methyl cellulose, hydroxypropylmethyl cellulose, waxes, phytate, cutin, saponins, suberin, tannins, chitosans, alginates, curdian, suberin, lignin, chitin, and the like, as well as combinations thereof.

In specific embodiments, the prebiotic comprises, alternatively consists essentially of, alternatively is, a fiber and/or a starch. In such embodiments, the fiber and/or a starch is not limited, and may be any exemplified by the general and specific examples of fibers and starch herein. In certain embodiments, the prebiotic comprises, alternatively consists essentially of, alternatively is, a resistant starch, i.e., a starch or starch digestion product that is not digested and/or absorbed in the stomach or small intestine of the subject, but instead is adapted to pass to the large intestine of the subject (e.g. for consumption, fermentation, and/or metabolism by the subject's gut microbiota). Examples of suitable resistant starches for use in or as the prebiotic, especially in embodiments where the subject is a mammal such as a human, typically include those categorized by one of skill in the art as category I resistant starch (e.g. starches that are physically inaccessible or indigestible by the subject, such as starches found in seeds, legumes, and unprocessed whole grains), category II resistant starch (e.g. starches resistant to enzymatic degradation in the subject's gut, including those that are enzymatically inaccessible due the conformation of the starch, such high amylose corn starch), category III resistant starch (e.g. starches formed when starch-containing foods such as pasta are cooked and cooled), and/or category IV resistant starch (e.g. starches chemically modified to resist digestion).

In particular embodiments, the active agent is or comprises the phytonutrient precursor compound. The phytonutrient precursor compound is not limited, and may be any compound that is derived from a plant source and capable of being microbially metabolized into the phytonutrient. In certain embodiments, the phytonutrient precursor compound is a raw plant material. In these or other embodiments, the phytonutrient precursor compound is a processed plant material, such as a compound or combination of compounds that was extracted, distilled, hydrolyzed, or otherwise derived from plant material, via natural and/or synthetic methods. In particular embodiments, the phytonutrient precursor compound is a partially metabolized plant material (e.g. produced from microbial metabolism/digestion). Such partially metabolized plant materials typically include an intermediate formed in the metabolic conversion of plant material to the phytonutrient. Many intermediates are typically formed in the conversion of plant material (e.g. a compound extracted therefrom) into its corresponding phytonutrient (e.g. post-metabolism). As such, the phytonutrient precursor compound may be any of such intermediates or combination of such intermediates. In this fashion, administration of the phytonutrient precursor compound to the subject may bypass microbial metabolic steps that would otherwise be needed to produce the phytonutrient (e.g. from raw plant material).

General examples of plants containing suitable phytonutrient precursor typically include fruits and/or berries, vegetables, nuts and/or seeds, beans, legumes, herbs and/or spices, and the like, or combinations thereof. Some specific examples of such plants include red onions, capers, citrus fruits, cranberries, apples, grapes, sweet potatoes, bilberries, black currants, pomegranate, red berries, walnuts, soy, flax or other seeds, cruciferous vegetables or other leafy greens, and/or green tea. Further examples of such plants may include whey, rice, wheat, pulses, peas, potatoes, fruit, buckwheat, and/or corn.

Examples of types of phytonutrient precursor compounds suitable for use in accordance with this disclosure typically include proteins, peptides, complex amino acids, lipids (e.g. fatty acids, sterols, prenols, saccharolipids, glycerolipids, glycerophospholipids, polyketides, sphingolipids, etc.), carotenoids, phenolic phytocompounds, alkaloids, glucosinolates, polysachharides, terpenes, betalains, polyacetylenes (e.g. falcarinols, falcarindiols, panaxydiols, oenanthetols, etc.), capsaicinoids (e.g. capsaicin, hihydrocapsaicin, homocapsaicin, nonivamides, etc.), allium compounds (e.g. methiin, propiin, isoalliin, etc.), lectins (e.g. concanavalins, ricins, agglutinins such as wheat germ agglutinins, peanut agglutinins, soybean agglutinins, etc.), organosulfur phytocompounds (e.g. isothiocyanates, indoles, allylic sulfur compounds, etc.), and the like, as well as derivatives, modifications, and combinations thereof. Some specific examples of carotenoid phytonutrient precursor compounds include carotenes (e.g. alpha-carotene, beta-carotene, etc.), cryptaxanthin, zeaxanthin, astaxanthin, lycopene, luteins, and the like, as well as derivatives, modifications, and combinations thereof. Some specific examples of phenolic phytonutrient precursor compounds include phenols, phenolic acids (e.g. benzoic and hydroxylbenzoinc acids, such as gallic acids, protocatechuic acids, vannilic acids, syringic acids, etc.; cinnamic and hydroxycinnamic acids, such as p-coumaric acid, caffeic acid, ferulic acid, sinapic acid, etc.), flavonoids, flavonols (e.g. quercetins, kaempferols, myricetins, galangins, fisetins, etc.), flavones (e.g. apigenins, chrysins, luteolins, etc.), flavanols (e.g. catechins, epicatechins, epigallocatechins, etc.), flavanones (e.g. eridictyol, hesperitin, naringenin, etc.), anthocyanidins (cyaniding, pelargonidin, delphinidin, peonidin, malvidin, etc.), proanthocyanidins, isoflavonoids (genistein, daidzein, glycitein, formononetin, etc.), dihydroflavonols, flavan-3-ols, flavonoids, isoflavones, tannins, acetophenones, phenylacetic acids, coumarins, bensophenones, zanthones, stilbenes, chalcones, lignans, secoiridoids, and the like, as well as derivatives, modifications, and combinations thereof. Some specific examples of alkaloid precursor compounds include ajmaline, berberine, caffeine, camptothecin, cocaine, codeine, hyoscyamine, irinolecan, morphine, nicotine, noscapine, oxycodone, oxymorphone, papaverine, and the like, as well as derivatives, modifications, and combinations thereof. Some specific examples of glucosinolate precursor compounds include glucoiberin, progoitrin, sinigrin, gluconapoleiferin, glucoraphanin, glucoalyssin, glucocapparin, glucobrassicin, neoglucobrassicin, glucosinalbin, glucotropaeolin, gluconasturtiin, and the like, as well as derivatives, modifications, and combinations thereof. Some specific examples of polysachharide precursor compounds include celluloses, hemicelluloses, arabinoxylans, arabingalactans, polyfructoses, polydextroses, methyl celluloses, inulins, oligofructans, oligosaccharides, gums, meilages, pectins, and the like, as well as derivatives, modifications, and combinations thereof. Some specific examples of terpene precursor compounds include cinerins, geraniols, calotropins, strigols, caulerpenynes, famesanes, squalanes, and the like, as well as derivatives, modifications, and combinations thereof. Some specific examples of betalain precursor compounds include betalain, betaxanthin, vulgaxanthin, miraxanthin, portulaxanthin, indicaxanthin, and the like, as well as derivatives, modifications, and combinations thereof.

In certain embodiments, the phytonutrient precursor compound comprises, alternatively consists essentially of, alternatively is, quercetin, cyanidin-3-glucoside, hesperidin, ellagic acid, daidzein (+), secoisolariciresinol diglucoside, glucosinolate, and/or epigallocatechin.

With regard to the examples of phytonutrient precursor compounds herein, modifications and/or derivatives of compounds may vary, and may be illustrated by metabolic and/or synthetic intermediates of such compounds, as well as naturally and/or synthetically modified compounds. For example, epicatechin gallate is an ester of gallic acid and epicatechin. As such, to illustrate the scope of some of the examples above, one of skill in the art will understand that epicatechin and epicatechin gallate may be considered derivatives and/or modifications of each other (e.g. via esterification or hydrolysis). Accordingly, it is to be appreciated that the specific examples of phytonutrient precursor compounds are not intended to be limiting, but rather illustrate that the method and composition of this disclosure is suitable for use with numerous phytonutrient precursor compounds.

In various embodiments, the phytofunctional composition comprises multiple active agents, which may each be independently selected. Typically, each active agent comprises, or alternatively is, at least one of the probiotics, prebiotics, and/or phytonutrient precursor compounds described above. However, in some embodiments, other active agents may be utilized in addition to the agent suitable for ameliorating the phytonutrient-producer status of the subject. In particular embodiments, the phytofunctional composition comprises a combination of the probiotic and the phytonutrient precursor compound. In some embodiments, the phytofunctional composition is free from, alternatively is substantially free from, the phytonutrient precursor compound. In specific embodiments, the phytofunctional composition is provided as a kit, where the kit includes a probiotic component and a phytonutrient precursor compound components. In such embodiments, the components of the kit may be administered together or separately (e.g. sequentially, in any order).

In certain embodiments, the method includes identifying an active agent to ameliorate or otherwise change the phytonutrient-producer status of the subject. For example, the identification of the active agent may be based on the phytonutrient-producer status of the subject, such as in a personalized treatment based on the subject's unique microbiome signature. However, the identification may be based on the phytonutrient-producer status of one or more hosts other than the subject. For example, in certain embodiments, identifying the active agent comprises performing a population study to determine the phytonutrient-producer status of various individuals among the population. In such embodiments, the population study may assess the phytonutrient-producer status of the individuals for any number of particular phytonutrients, such as 1, 2, 3, 4, 5, 6, 7, 8, 9, 10, or more particular phytonutrients (e.g. via mass assay), and classify each individual as a producer or non-producer (or poor producer) with respect to each of the particular phytonutrients assessed (collectively, the individuals' "phytonutrient production profile"). The active agent(s) may then be selected to ameliorate or change the production status of each individual assessed with respect to each of the particular phytonutrients not being adequately produced or metabolized. In this fashion, the active agent(s) of the phytofunctional composition may be selected based on certain deficiencies common to various individuals among the population, irrespective of the subject's own microbiome function. As such, the present method provides for both personalized and generalized treatment options, and the phytofunctional composition may present increased efficacy and/or effectiveness as compared to treatments not taking into account the phytonutrient production profile across a population.

In some embodiments, identifying the active agent may comprise conducting a trial, study, and/or a model-based experiment, which may be exemplified by human intervention trials, experiments with other animal models (e.g. humanized mouse models), and/or in-vitro colonic models. For example, in certain embodiments, identifying the active agent comprises conducting a human intervention study. In such embodiments, the human intervention study may comprise: (i) collecting from participating subjects fecal and/or colonic microbiome samples and related sequence data (e.g. metagenomic, 16S RNA, etc., collectively "microbiome genetic data"); (ii) administering to the participating subjects a phytonutrient precursor compound; (iii) collecting blood, fecal, and/or urinary samples from the participating subjects; (iv) analyzing the blood, fecal, and/or urinary samples for the conversion of the phytonutrient precursor compound into a phytonutrient; (v) analyzing the microbiome genetic data related to genes responsible for the conversion of the phytonutrient precursor compound into the phytonutrient; (vi) identifying genetic differences between producer and non-producers of the phytonutrient; (vii) identifying an active agent (e.g. a probiotic, prebiotic, and/or phytonutrient precursor compound) to ameliorate the producer status of the participating subjects; (viii) administering to the participating subjects a phytofunctional composition comprising the identified active agent, optionally in combination with the phytonutrient precursor compound; and (ix) monitoring the conversion of the phytonutrient precursor compound to the phytonutrient. Similar work streams comprising in-vitro colon models, intestinal models, humanized mice models (e.g. those utilizing germ free mice that have been gavaged with human microbiota samples), etc.

In addition to the active agent, the phytofunctional composition may comprise any number of additional ingredients/components. For example, in some embodiments the phytofunctional composition comprises an additive component, which may comprise one or more additives. Examples of suitable additives for use in the additive component include amino acids, peptides, proteins, lipids, vitamins, carbohydrates, nucleic acids, minerals, anabolic nutrients, antioxidants, probiotic bacterial strains, lipotropic agents, extracts, concentrates, oils, gums, fiber, starch, and the like, and combinations thereof. In certain embodiments, the phytofunctional composition comprises the additive component, and the additive component comprises an amino acid, a peptide, a protein, a lipid, a vitamin, a carbohydrate, a nucleic acid, a mineral, an anabolic nutrient, an antioxidant, a probiotic bacterial strain, a lipotropic agent, or a combination thereof. In these or other embodiments, the additive component comprises a flavoring agent, a dye, a flow modifier, a preservative, a filler, a binder, a dispersing agent, a carrier, a supplemental nutrient, or any combination thereof. In particular embodiments, the additive component comprises a carrier, such as a consumable, nutritional, and/or pharmaceutical carrier, or a combination thereof. In certain embodiments, the additive component comprises an animal-, algal-, and/or fungal-based protein, peptide, and/or complex amino acid, such as an egg protein isolate.

In addition to those additives listed above, specific examples of additives suitable for use in the additive component include pea protein isolate, isomalto-oligosaccharide, rice protein concentrate, 2'-fucosyllactose powder, flaxseed, organic cane sugar, natural flavors, high oleic sunflower oil, L-lysine HCl, medium chain triglycerides, L-leucine, Silica, L-valine, L-alanyl-L-glutamine, L-isoleucine, xanthan gum, vitamins, minerals, zinc gluconate, ascorbic acid, manganese gluconate, alpha tocopheryl acetate, copper gluconate, D-biotin, retinyl palmitate, niacinamide, cholecalciferol, calcium pantothenate, chromium picolinate, pyridoxine HCl, riboflavin, potassium iodide, thiamin HCl, calcium L-5-methyltetrahydrofolate, selenomethionine, and methylcobalamin, Luo Han Guo fruit (monk fruit) extract, vanilla, rosemary extract, cocoa powder, vitamin E, thiamin, riboflavin, niacin, vitamin B6, folate, vitamin B12, biotin, pantothenic acid, phosphorus, iodine, magnesium, zinc, selenium, copper, manganese, and the like, and combinations thereof. Of course, components aside from the additive component may also be utilized in the phytofunctional composition.

The phytofunctional composition can be administered to the subject orally, but other routes of administration may also be utilized. When formulated for oral administration, the phytofunctional composition may be presented in discrete units (e.g. capsules, cachets, lozenges, tablets, etc.) that each containing a predetermined amount of the phytofunctional composition (e.g. a recommended dose). However, the phytofunctional composition may compose any form, such as a dry powder, a solution, a suspension, an emulsion, or the like. In certain embodiments, the phytofunctional composition is a dry powder. In some embodiments, the phytofunctional composition is adapted to be consumed as a liquid. For example, the phytofunctional composition may be a dry powder that is combined with a consumable liquid (e.g. water) to form a consumable liquid solution, suspension, or emulsion comprising the phytofunctional composition.

In certain embodiments, the phytofunctional composition may be adapted to be mixed with a foodstuff or beverage. The term "foodstuff" is used herein to refer to a material that may be used as a food. As such, in certain instances the term foodstuff is used to describe a composition that may be consumed (e.g. by eating) by a living organism (e.g. a mammal), such as for nourishment and/or sustenance. Likewise, the term "beverage" as used herein refers to a potable liquid or other non-solid composition. As such, in certain instances the term beverage is used to describe a non-solid (e.g. liquid, slurry, suspension, etc.) composition that may be consumed by a living organism for nourishment and/or sustenance. As such, in particular instances the terms "beverage" and "foodstuff" may overlap. In certain instances, the term "nutritional composition" is used to describe a foodstuff and/or beverage formulation that can be eaten or drunk by a human subject for nutrition. Accordingly, in some embodiments, the phytofunctional composition is, alternatively is a component of, a foodstuff or beverage.

In these or other embodiments, the phytofunctional composition may be further defined as a food additive. As used herein, the term "food additive" refers to an ingredient, additive, component, or supplement suitable for incorporation in a foodstuff and/or beverage to confer a technical, nutritional, and/or health benefit (i.e., a function) to a host that consumes the foodstuff and/or beverage. Accordingly, such benefits may be closely related to the presence of the phytonutrient in the subject. The food additive can be added to different types of food including, but not limited to, medical foods, dietetic foods, and supplements. Certain aspects of the present embodiments can include the use of the phytofunctional composition as a food additive, and the use of the phytofunctional composition in methods of preparing foodstuffs and/or beverages.

In general, when utilized as a component of a foodstuff or beverage, the foodstuff or beverage comprises an admixture of the phytofunctional composition with one or more feed products, liquids, supplements, or combinations thereof. However, in certain embodiments, the phytofunctional composition may itself be further defined as a foodstuff or beverage composition, depending on the quantity, nature, and identity of individual additives and components present in the phytofunctional composition, such as those described above. Thus, it is to be appreciated that the embodiments described herein with respect to the phytofunctional composition are intended to equally encompass the foodstuff or beverage, a food or beverage product, and/or a food supplement comprising the phytofunctional composition. Accordingly, any amounts and/or examples of such components described herein with respect to the phytofunctional composition itself may equally apply to the foodstuff or beverage comprising the phytofunctional composition.

In some embodiments, the foodstuff or beverage comprising the phytofunctional composition is further defined as a nutritional composition. In these or other embodiments, the nutritional composition is in the form of a dry food concentrate, which may be mixed with liquid or food and subsequently consumed. It is to be appreciated that the nutritional composition is distinguished from a vaccine, and the phytofunctional compositions described herein may be free, alternatively substantially free, from a vaccine.

In certain embodiments, the phytofunctional composition may be further defined as a nutritional supplement, or as a complete nutritive. As used herein, the term "supplement" relates to a nutritional supplement which is a concentrated source of nutrient or alternatively other substances with a nutritional or physiological effect whose purpose is to supplement the normal diet. For example, the phytofunctional composition may be formulated to provide a mammal (e.g. a human), via consumption of the phytofunctional composition, with at least 5%, alternatively at least 10%, alternatively at least 25%, alternatively at least 50%, alternatively at least 75%, alternatively at least 90%, of daily calories required by the mammal. However, it is to be appreciated that a daily calorie requirement is dependent on several factors, including the gender, height, and/or age of the mammal, and thus the percentage of caloric requirement provided by the phytofunctional composition will be dependent on the particular person consuming the nutritional composition. For example, a 30 year old human male of 80 kg body weight and 180 cm height has a daily calorie requirement of around 2900 cal (calories) to maintain his body weight whereas a 30 year old human female of 55 kg body weight and 165 cm height has a daily calorie requirement of around 2100 cal to maintain her body weight. In some embodiments, the foodstuff or beverage is further defined as a medical food. As such, it is to be appreciated that the medical food comprises the phytofunctional composition, and may be the same as or different from the nutritional composition described above. As used herein, the term "medical food" is typically used to refer to a food for a special dietary use, such as a food formulated for dietary management of a medical condition (e.g. based upon scientific or medical evaluation). However, it is to be appreciated that the term "medical food" may have one or more particular definitions depending on, for example, geographic location, specific use, regulatory agency, and the like. For example, in certain cases, the term medical food may be defined as a food which is formulated to be consumed or administered enterally under the supervision of a physician and which is intended for the specific dietary management of a disease or condition for which distinctive nutritional requirements, based on recognized scientific principles, are established by medical evaluation (see, e.g. section 5(b) of the Orphan Drug Act (21 U.S.C. 360ee (b) (3)), which is incorporated herein by reference). In these or other instances, the term medical food may be defined as a food for special dietary use as a food that has been specially processed or formulated to meet the particular requirements of a person: (a) in whom a physical or physiological condition exists as a result of a disease, disorder, or injury; or (b) for whom a particular effect, including but not limited to weight loss, is to be obtained by a controlled intake of food (see, e.g. section 8.24.001 of the Canadian Food and Drug Regulations (FDR, C.R.C., c. 870)(as amended 13 Jun. 2017)), which is incorporated herein by reference).

In certain embodiments, the phytofunctional composition is further defined as an animal food. In such embodiments, the phytofunctional composition is typically formulated for ingestion by one or more non-human animals, such as livestock including cattle, swine, horses, sheep, goats, poultry, and fish, domesticated companionship species such as dogs, cats, fish, and rodents, undomesticated wildlife such as deer, moose, elk, migratory, and non-migratory fowl, those non-human animals described herein, and combinations thereof. In certain instances, administering the phytofunctional composition as the animal food to a non-human subject (e.g. an animal) may result in an increased yield in one or more commodities produced by the host, such as eggs, meat, milk, wool, etc.

The following examples are intended to illustrate the invention and are not to be viewed in any way as limiting the scope of the invention.

Example 1: Phytonutrient Producer Status

The phytonutrient producer status of 11 human subjects ("Subjects 1-11", or "S1"-"S11", respectively) was assessed by determining the microbial metabolism of various phytonutrient precursor compounds. In particular, an intestinal microbiota-representing microarray was constructed as described in by culturing in-vitro fermentations of fecal samples obtained from each donor, as described in S. E. Ladirat et al., High-throughput analysis of the impact of antibiotics on the human intestinal microbiota composition, Journal of Microbiological Methods 92 (2013), pp. 387-397, which is incorporated by reference herein, with selected phytonutrient precursor compounds. The metabolism of the phytonutrient precursor compound in each assay was then determined via monitoring conversion (+), partial conversion (±), or no conversion (−) of the phytonutrient precursor compound over time. The results of the microarray and the various phytonutrient precursor compounds used therein are set forth in Table 1 below.

TABLE 1

Phytonutrient Producer Status

| Phytonutrient Precursor Compound | S1 | S2 | S3 | S4 | S5 | S6 | S7 | S8 | S9 | S10 | S11 |
|---|---|---|---|---|---|---|---|---|---|---|---|
| Hesperidin | + | + | + | + | ± | + | + | + | + | + | + |
| Epigallocatechol | + | + | ± | + | + | + | + | + | + | + | + |
| Secoisolariciresinol diglucoside | + | + | ± | + | + | ± | ± | ± | + | + | + |
| Quercetin | − | + | + | + | − | + | + | − | − | + | − |
| Cyanidin-3-glucoside | ± | ± | + | ± | ± | + | + | ± | + | + | + |
| Ellagic acid | ± | ± | ± | − | − | − | − | ± | − | ± | − |
| Daidzein | − | − | − | − | − | − | − | − | − | − | − |

As shown in Table 1, all but two of the subjects (S7 and S11) presented unique metabolic fingerprints, with varying abilities to metabolize the phytonutrient precursor compounds utilized.

Example 2: Identifying Active Compounds for Mediating Phytonutrient Producer Status Various probiotics were assessed for ability to metabolize phytonutrient precursor compounds in order to identify active compounds for use in the phytofunctional composition. In particular, bacterial strains were obtained and stored at −80° C. The strains were then thawed, and the resulting cell suspensions plated onto media plates with an inoculation needle and incubated for 3-5 days. The bacterial strains, media, and culture conditions are set forth in Table 2 below.

TABLE 2

Probiotic Bacteria for Active Agent

| Culture | Genus | Strain | Media/Agar | Conditions |
|---|---|---|---|---|
| #1 | Bifidobacterium animalis lactis | HN019 | RCM | Anaerobic at 37° C. |
| #2 | Bifidobacterium animalis lactis | B420 | RCM | Anaerobic at 37° C. |
| #3 | Bifidobacterium animalis lactis | Bl-04 | RCM | Anaerobic at 37° C. |
| #4 | Bifidobacterium animalis lactis | Bi-07 | RCM | Anaerobic at 37° C. |
| #5 | Bifidobacterium breve | Bb-03 | RCM | Anaerobic at 37° C. |
| #6 | Bifidobacterium longum longum | Bl-05 | RCM | Anaerobic at 37° C. |
| #7 | Bifidobacterium bifidum | Bb-06 | RCM | Anaerobic at 37° C. |
| #8 | Bifidobacterium longum infantis | Bi-26 | RCM | Anaerobic at 37° C. |
| #9 | Bifidobacterium animalis lactis | Bb-12 | RCM | Anaerobic at 37° C. |
| #10 | Bifidobacterium | Unknown | RCM | Anaerobic at 37° C. |
| #11 | Lactococcus lactis lactis | Ll-23 | LM17/BHI | Aerobic at 30° C. |
| #12 | Streptococcus thermophilus | St-21 | LM17/MRSpH 6.8 | Microaerophilic at 37° C. |
| #13 | Lactobacillus acidophilus | NCFM | MRS | Aerobic at 37° C. |
| #14 | Lactobacillus rhamnosus | HN001 | MRS | Aerobic at 37° C. |
| #15 | Lactobacillus paracasei | Lpc-37 | MRS | Aerobic at 37° C. |
| #16 | Lactobacillus plantarum | Lp-115 | MRS | Aerobic at 37° C. |
| #17 | Lactobacillus acidophilus | La-14 | MRS | Aerobic at 37° C. |
| #18 | Lactobacillus casei | Lc-11 | MRS | Aerobic at 37° C. |
| #19 | Lactobacillus rhamnosus | Lr-32 | MRS | Aerobic at 37° C. |
| #20 | Lactobacillus salivarius | Ls-33 | MRS | Aerobic at 37° C. |
| #21 | Lactobacillus bulgaricus | Lb-87 | MRS/BHI | Aerobic at 37° C. |
| #22 | Lactobacillus brevis | Lbr-35 | MRS | Aerobic at 37° C. |
| #23 | Lactobacillus reuteri | 1E1 | MRS | Aerobic at 37° C. |
| #24 | Lactobacillus fermentum | SBS-1 | MRS | Aerobic at 37° C. |
| #25 | Lactobacillus gasseri | Lg-36 | MRS | Aerobic at 37° C. |
| #26 | Lactobacillus rhamnosus | GG | MRS | Aerobic at 37° C. |
| #27 | Weissella confusa | DGCC2236 | MRS | Aerobic at 30° C. |
| #28 | Saccharomyces cerevisiae | DGCC9624 | GG | Aerobic at 25° C. |

After three days, a colony was taken from each culture and plated again onto another agar plate, to check for purity. The cultures were then incubated again for another 3-5 days at the optimal culture conditions, at which time another colony was taken and plated onto an agar plate. The cultures were then incubated for 3-5 days under anaerobic conditions at 37° C., to adapt the strains to the screen culture conditions.

At 48 and 24 hours before the experiment, colonies were transferred to media (MSRB, BHIB, GGB, MRSph6.8B and RCMB, maintained anaerobic for at least 48 hours before inoculation) and incubated for 48 or 24 hours under anaerobic conditions at 37° C., 450 rpm on a shaking plate.

Various phytonutrient precursor compounds were dissolved in DMSO to a concentration of 10 mg/ml. 24 hours before the experiment, the compounds were mixed together and diluted to a concentration of 0.5 mg/ml in DMSO. In triplicate, 10 µl compound mix and DMSO (control) were transferred to a 2.0 mL deep well plate, and the resulting plates sealed with a breathable seal and stored anaerobically in a jar at 4° C.

At the day of experiment, with all steps performed under anaerobic conditions, $OD_{600}$ of each strain was measured out and diluted in media to an $OD_{600}$ of 0.5. The strains were then diluted 100× in culture media, and 990 µL of the diluted strain medium mix added to the 10 µL compound/DMSO in the prepare plate wells. The plates were then incubated for 48 hours under anaerobic conditions at 37° C., 450 rpm on a shaking plate.

Samples (100 µL) were collected from each well at t=0, 24 and 48 hours, and subjected to metabolite analysis (LC-MS) to determine consumption ("yes"), partial metabolism ("?"), or no conversion ("no") of the phytonutrient precursor compound over time, the results of which are set forth in Tables 3 and 4 below.

TABLE 3

Select Metabolic Activity of Probiotic Bacteria for Active Agent

| Culture | Quercetin | Cyanidin-3-glucoside | Epigallocatechin | Hesperidin |
|---------|-----------|----------------------|------------------|------------|
| #1  | no | no  | no  | no  |
| #2  | no | no  | no  | no  |
| #3  | no | no  | no  | no  |
| #4  | no | no  | no  | no  |
| #5  | no | yes | no  | no  |
| #6  | no | no  | no  | no  |
| #7  | no | yes | no  | no  |
| #8  | no | yes | no  | no  |
| #9  | no | no  | no  | no  |
| #10 | no | yes | no  | yes |
| #11 | no | ?   | no  | no  |
| #12 | no | yes | no  | no  |
| #13 | no | yes | no  | no  |
| #14 | no | yes | yes | no  |
| #15 | no | yes | ?   | no  |
| #16 | no | yes | ?   | no  |
| #17 | no | yes | no  | no  |
| #18 | no | yes | no  | no  |
| #19 | no | yes | yes | no  |
| #20 | no | yes | no  | no  |
| #21 | no | yes | no  | no  |
| #22 | no | yes | no  | no  |
| #23 | no | yes | no  | no  |
| #24 | no | yes | no  | no  |
| #25 | no | yes | no  | ?   |
| #26 | no | yes | no  | ?   |
| #27 | no | yes | no  | no  |
| #28 | no | yes | no  | no  |

TABLE 4

Select Metabolic Activity of Probiotic Bacteria for Active Agent

| Culture | Ellagic Acid | Daidzein | Secoisolariciresinol diglucoside |
|---------|--------------|----------|----------------------------------|
| #1  | no | no | no |
| #2  | no | no | no |
| #3  | no | no | no |
| #4  | no | no | no |
| #5  | no | no | no |
| #6  | no | no | no |
| #7  | no | no | no |
| #8  | no | no | no |
| #9  | no | no | no |
| #10 | ?  | no | no |
| #11 | ?  | no | no |
| #12 | no | no | no |
| #13 | no | no | no |
| #14 | no | no | no |
| #15 | no | no | no |
| #16 | no | no | no |
| #17 | no | no | no |
| #18 | no | no | no |
| #19 | no | no | no |
| #20 | no | no | no |
| #21 | no | no | no |
| #22 | no | no | no |
| #23 | no | no | no |
| #24 | no | no | no |
| #25 | no | no | no |
| #26 | no | no | no |
| #27 | no | no | no |
| #28 | no | no | no |

In Tables 3 and 4 above, a "yes" was recorded to indicate that the corresponding phytonutrient precursor compound (i.e., quercetin, cyanidin-3-glucoside, epigallocatechin, hesperidin, ellagic acid, daidzein (+), or secoisolariciresinol diglucoside) was fully metabolized at 24 and/or 48 hrs. A "no" was recorded to indicate that no metabolism of the corresponding phytonutrient precursor compound was observed 24 or 48 hrs. A "?" was recorded to indicate that partial metabolism/consumption of the corresponding phytonutrient precursor compound was observed at 24 and/or 48 hrs.

A mixture of each phytonutrient precursor compound and its metabolite mixture was prepared and diluted in spent media to validate the separation and sensitivity at lower concentrations observable via LC-MS. The phytonutrient precursor compounds were all well detectable at ~2 µg/mL (1:10 dilution) using 50:50(%) spent media/formic acid.

As shown in Tables 3 and 4, select probiotic strains may be used in, or as, the active agent of the phytofunctional composition to microbially metabolize certain phytonutrient precursor compounds. These active agents may be readily determined via microarray in a convenient and efficient fashion for a variety of phytonutrient precursor compounds. Moreover, as the phytonutrient precursor compounds are not universally metabolized, as demonstrated in Example 1 above, the active agent may selected based on a producer status of a subject, e.g. via an individualized metabolic panel.

As will be understood by those of skill in the art, this disclosure provides, in first embodiment, a method of changing a phytonutrient producer status of a subject, where the method comprises: administering a phytofunctional composition to the subject, wherein the phytofunctional composition comprises a phytonutrient precursor compound, and an active agent comprising a probiotic and/or a prebiotic, where the active agent is adapted to mediate production of a preselected phytonutrient from the phytonutrient precursor compound in the gastrointestinal tract of the subject; thereby changing the phytonutrient producer status of the subject.

In a second embodiment, the method of the first embodiment further comprises identifying the phytonutrient producer status of the subject by assessing a level of the preselected phytonutrient or a preselected phytonutrient precursor compound within the subject, prior to administering the phytofunctional composition thereto.

In a third embodiment, the method of the first or second embodiment is further characterized by identifying the phytonutrient producer status of the subject being performed in vitro, by: obtaining a sample from the gastrointestinal tract of the subject; and quantifying an amount of the preselected phytonutrient in the sample.

In a fourth embodiment, the method of the third embodiment is further characterized by the sample being further defined as a fecal sample.

In a fifth embodiment, the method of the fourth embodiment further comprises culturing the fecal sample in the presence of the preselected phytonutrient precursor compound prior to quantifying the amount of the preselected phytonutrient in the sample.

In a sixth embodiment, the method of any one of the first through fifth embodiments, sequentially, is further characterized by the preselected phytonutrient being further defined as a first preselected phytonutrient, wherein identifying the phytonutrient producer status further comprises assessing a level of at least one of a second preselected phytonutrient and a second preselected phytonutrient precursor compound within the subject, where the second preselected phytonutrient is a microbial metabolite of the second phytonutrient precursor compound, and wherein the phytofunctional composition is adapted to mediate production of the second preselected phytonutrient in the gastrointestinal tract of the subject.

In a seventh embodiment, the method of sixth embodiment is further characterized by the first and second preselected phytonutrients not being metabolically related.

In an eighth embodiment, the method of any one of the first through seventh embodiments is further characterized by: (i) the preselected phytonutrient being a microbial metabolite of the phytonutrient precursor compound; (ii) mediating the production of the preselected phytonutrient being further defined as increasing a level of microbial metabolism producing the preselected phytonutrient in the gastrointestinal tract of the subject; or (iii) both (i) and (ii).

In a ninth embodiment, the method of any one of the first through eighth embodiments is further characterized by the active agent of the phytofunctional composition comprising the probiotic.

In a tenth embodiment, the method of ninth embodiment is further characterized by the probiotic comprises a bacterial strain capable of metabolizing the phytonutrient precursor compound to increase a level of the preselected phytonutrient in the gastrointestinal tract of the subject.

In an eleventh embodiment, the method of tenth embodiment is further characterized by the probiotic comprising: (i) a *Bifidobacterium* spp.; (ii) a *Lactobacillus* spp.; or (iii) both (i) and (ii).

In a twelfth embodiment, the method of any one of the first through eleventh embodiments is further characterized by changing the phytonutrient producer status of the subject being further defined as increasing the production of the preselected phytonutrient in the gastrointestinal tract of the subject.

In a thirteenth embodiment, the method of any one of the first through twelfth embodiments is further characterized by the phytofunctional composition being administered to the subject orally.

In a fourteenth embodiment, the method of any one of the first through thirteenth embodiments is further characterized by the phytofunctional composition being administered to the subject in a dosage formulation over a treatment period.

In a fifteenth embodiment, the method the fourteenth embodiments is further characterized by the amount and timing of each dose being selected to maintain the changed phytonutrient producer status for a majority of the treatment period.

In a sixteenth embodiment, the method of any one of the first through fifteenth embodiments is further characterized by the phytonutrient precursor compound comprising: (i) quercetin; (ii) cyanidin-3-glucoside; (iii) epigallocatechin; (iv) hesperidin; (v) ellagic acid; (vi) secoisolariciresinol diglucoside; (vii) a metabolite of any of (i)-(vi); or (viii) any combination of (i)-(vii).

In a seventeenth embodiment, the method of any one of the first through sixteenth embodiments is further characterized by the phytonutrient being preselected from 2,4,6-trihydroxybenzoic acid, parargonidin-3-O-glucoside, hesperitin, urolithin A, hydroferulic acid hydrocaffeic acid, and dihydroxyphenylacetic acid.

As will also be understood by those of skill in the art, this disclosure further provides, in an eighteenth embodiment, a phytofunctional composition for mediating a subject's microbial metabolism, the phytofunctional composition comprising a phytonutrient precursor compound, and an active agent comprising a probiotic and/or a prebiotic, where the active agent is adapted to mediate production of a preselected phytonutrient from the phytonutrient precursor compound in the gastrointestinal tract of a subject.

In a nineteenth embodiment, the phytofunctional composition of the eighteenth embodiment is further characterized by the phytonutrient precursor compound comprising: (i) quercetin; (ii) cyanidin-3-glucoside; (iii) epigallocatechin; (iv) hesperidin; (v) ellagic acid; (vi) secoisolariciresinol diglucoside; (vii) a metabolite of any of (i)-(vi); or (viii) any combination of (i)-(vii).

In a twentieth embodiment, the phytofunctional composition of the eighteenth or nineteenth embodiment is further characterized by the active agent of the phytofunctional composition comprising the probiotic.

In a twenty first embodiment, the phytofunctional composition of the twentieth embodiment is further characterized by the probiotic comprising a bacterial strain capable of metabolizing the phytonutrient precursor compound to increase a level of the preselected phytonutrient in the gastrointestinal tract of a subject.

In a twenty second embodiment, the phytofunctional composition of the twentieth or twenty first embodiment is further characterized by the probiotic comprising: (i) a *Bifidobacterium* spp.; (ii) a *Lactobacillus* spp.; or (iii) both (i) and (ii).

In a twenty third embodiment, the phytofunctional composition of any one of the eighteenth through twenty second embodiments is further characterized by the phytonutrient being preselected from 2,4,6-trihydroxybenzoic acid, parargonidin-3-O-glucoside, hesperitin, urolithin A, hydroferulic acid hydrocaffeic acid, and dihydroxyphenylacetic acid.

In a twenty third embodiment, the phytofunctional composition of any one of the eighteenth through twenty third embodiments is further characterized by the phytonutrient precursor compound being further defined as a first phytonutrient precursor compound and the preselected phytonutrient being further defined as a first preselected phytonutrient, wherein the phytofunctional composition further comprises a second phytonutrient precursor compound, and wherein the active agent is adapted to mediate production of the first preselected phytonutrient from the first phytonutrient precursor compound and a second preselected phytonutrient from the second phytonutrient precursor compound in the gastrointestinal tract of the subject.

The terms "comprising" or "comprise" are used herein in their broadest sense to mean and encompass the notions of "including," "include," "consist(ing) essentially of," and "consist(ing) of. The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "-" in a range of values is "to" or "through"; a ">" is "above" or "greater-than"; a "≥" is "at least" or "greater-than or equal to"; a "<" is "below" or "less-than"; and a "≤" is "at most" or "less-than or equal to." On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology that has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

What is claimed is:

1. A method of changing a phytonutrient-producer status of a subject, the method comprising:
   identifying the phytonutrient-producer status of the subject by assessing a level of a preselected phytonutrient or a preselected phytonutrient precursor compound within the subject; and
   administering a phytofunctional composition to the subject, the phytofunctional composition comprising:
   a phytonutrient precursor compound, and
   an active agent comprising a probiotic, the active agent being adapted to mediate production of a preselected phytonutrient from the phytonutrient precursor compound in the gastrointestinal tract of the subject, thereby changing the phytonutrient-producer status of the subject;
   wherein the probiotic comprises a bacterial strain capable of metabolizing the phytonutrient precursor compound to increase the level of the preselected phytonutrient in the gastrointestinal tract of the subject.

2. The method of claim 1, wherein identifying the phytonutrient-producer status of the subject is performed in vitro and comprises: obtaining a sample from the gastrointestinal tract of the subject; and quantifying an amount of the preselected phytonutrient in the sample.

3. The method of claim 2, wherein the sample is further defined as a fecal sample, and the method further comprises culturing the fecal sample in the presence of the preselected phytonutrient precursor compound prior to quantifying the amount of the preselected phytonutrient in the sample.

4. The method of claim 1, wherein the preselected phytonutrient is further defined as a first preselected phytonutrient;
   wherein identifying the phytonutrient-producer status further comprises assessing a level of at least one of a second preselected phytonutrient and a second preselected phytonutrient precursor compound within the subject, where the second preselected phytonutrient is a microbial metabolite of the second phytonutrient precursor compound;
   wherein the phytofunctional composition is adapted to mediate production of the second preselected phytonutrient in the gastrointestinal tract of the subject; and
   wherein the first and second preselected phytonutrients are not metabolically related.

5. The method of claim 1, wherein:
   (i) the preselected phytonutrient is a microbial metabolite of the phytonutrient precursor compound;
   (ii) mediating the production of the preselected phytonutrient is further defined as increasing a level of microbial metabolism producing the preselected phytonutrient in the gastrointestinal tract of the subject; or
   (iii) both (i) and (ii).

6. The method of claim 1, wherein the probiotic comprises: (i) a *Bifidobacterium* spp.; (ii) a *Lactobacillus* spp.; or (iii) both (i) and (ii).

7. The method of claim 1, wherein changing the phytonutrient-producer status of the subject is further defined as increasing the production of the preselected phytonutrient in the gastrointestinal tract of the subject.

8. The method of claim 1, wherein the phytofunctional composition is administered to the subject orally.

9. The method of claim 1, wherein the phytofunctional composition is administered to the subject in a dosage formulation over a treatment period, where the amount and timing of each dose is selected to maintain the changed phytonutrient-producer status for a majority of the treatment period.

10. The method of claim 1, wherein the phytonutrient precursor compound is provided in the phytofunctional composition as a component of a plant extract.

11. The method of claim 1, wherein the phytonutrient precursor compound comprises: (i) quercetin; (ii) cyanidin-3-glucoside; (iii) epigallocatechin; (iv) hesperidin; (v) ellagic acid; (vi) secoisolariciresinol diglucoside; (vii) a metabolite of any of (i)-(vi); or (viii) any combination of (i)-(vii).

12. The method of claim 1, wherein the phytonutrient is preselected from 2,4,6-trihydroxybenzoic acid, parargonidin-3-O-glucoside, hesperitin, urolithin A, hydroferulic acid, hydrocaffeic acid, and dihydroxyphenylacetic acid.

13. The method of claim 1, wherein identifying the phytonutrient-producer status of the subject by assessing a level of a preselected phytonutrient or a preselected phytonutrient precursor compound within the subject comprises urinalysis, fecal analysis, blood plasma analysis, tissue analysis, saliva analysis, or combinations thereof.

14. A method of increasing phytonutrient production of a subject, the method comprising the following steps:
    determining a phytonutrient-producer status and level of phytonutrients within the subject to identify phytonutrients that are at a low level via;
        obtaining a microbiota sample from the subject,
        culturing the microbiota sample to produce metabolic products from the phytonutrients,
        monitoring the metabolic products from the phytonutrients to determine a metabolic fingerprint, and
        analyzing the metabolic fingerprint to determine which of the phytonutrients are not metabolized by the subject;
    selecting probiotics that metabolize the phytonutrients that are not metabolized; and
    administering the phytonutrients and the selected probiotics that metabolize the phytonutrient to the subject thereby increasing the level and production of the metabolized phytonutrients in the subject.

15. The method of claim 14, wherein culturing the microbiota sample comprises fermenting the microbiota sample obtained from the subject.

16. The method of claim 14, wherein monitoring the metabolic products comprises monitoring presence and, optionally, an amount of phytonutrients produced.

17. The method of claim 14, wherein obtaining the microbiota sample is further defined as obtaining a fecal sample from the subject.

18. The method of claim 14, wherein determining the phytonutrient-producer status of the subject is further defined as comparing a biological concentration and/or excretion amount of a phytonutrient of the subject against commensurate measurements obtained from other subjects.

19. The method of claim 14, wherein:
    (I) monitoring the metabolic products is further defined as monitoring conversion, partial conversion, or no conversion of a phytonutrient precursor compound over time;
    (II) monitoring the metabolic products comprises analyzing one or more of the following phytonutrient precursor compounds: (i) quercetin; (ii) cyanidin-3-glucoside; (iii) epigallocatechin;
    (iv) hesperidin; (v) ellagic acid; (vi) secoisolariciresinol diglucoside; and (vii) a metabolite of any of (i)-(vi); or
    (III) both (I) and (II).

20. The method of claim 14, wherein the phytonutrient is preselected from 2,4,6-trihydroxybenzoic acid, parargonidin-3-O-glucoside, hesperitin, urolithin A, hydroferulic acid, hydrocaffeic acid, and dihydroxyphenylacetic acid.

* * * * *